United States Patent
Venturino et al.

(10) Patent No.: US 6,630,096 B2
(45) Date of Patent: Oct. 7, 2003

(54) MULTI-STAGE FORMING DRUM COMMUTATOR

(75) Inventors: Michael Barth Venturino, Appleton, WI (US); Derek Paul Murphy, Menasha, WI (US); Susan Joan Daniels, Neenah, WI (US); Joseph Michael Kugler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 210 days.

(21) Appl. No.: 09/947,128

(22) Filed: Sep. 4, 2001

(65) Prior Publication Data

US 2003/0042660 A1 Mar. 6, 2003

(51) Int. Cl.[7] .............................. A61F 13/15; B27N 3/14
(52) U.S. Cl. ....................................... 264/518; 425/83.1
(58) Field of Search .......................... 264/518; 425/83.1

(56) References Cited

U.S. PATENT DOCUMENTS

| | | | |
|---|---|---|---|
| 4,388,056 A | 6/1983 | Lee et al. ................... | 425/83.1 |
| 4,666,647 A | 5/1987 | Enloe et al. ................ | 264/121 |
| 4,761,258 A | 8/1988 | Enloe ......................... | 264/518 |
| 4,859,388 A | 8/1989 | Peterson et al. ............ | 264/121 |
| 4,904,440 A | 2/1990 | Angstadt .................... | 264/517 |
| 4,927,582 A | 5/1990 | Bryson ....................... | 264/113 |
| 5,004,579 A | 4/1991 | Wislinski et al. ........... | 264/517 |
| 5,772,813 A | 6/1998 | Bitowft et al. ............. | 156/62.4 |
| 5,866,173 A | 2/1999 | Reiter et al. ............... | 425/80.1 |
| 5,983,457 A | 11/1999 | Toney et al. ................ | 19/308 |
| 6,330,735 B1 | 12/2001 | Hahn et al. ................. | 19/296 |

FOREIGN PATENT DOCUMENTS

DE 3508344 A1 9/1986
WO WO 85/04366 A1 10/1985

OTHER PUBLICATIONS

Patent Abstracts of Japan 2000178866: Description of Machida Yoshinobu / Kao Corp., "Production of Fibrous Form and Production Unit Therefor."

*Primary Examiner*—Mary Lynn Theisen
(74) *Attorney, Agent, or Firm*—Paul Y. Yee; John L. Brodersen

(57) ABSTRACT

A method and apparatus (20) for forming a fibrous web (50) includes a movable, foraminous forming surface (22) and a substantially stationary, vacuum-commutator duct system (24) which is located substantially subjacent the forming surface (22). The vacuum-commutator duct system (24) has an entrance opening (26) that changes in configuration along a longitudinal dimension (30) of the entrance opening (26).

20 Claims, 12 Drawing Sheets

MULTI-STAGE FORMING DRUM COMMUTATOR

FIELD OF THE INVENTION

This invention generally relates to apparatus and method for forming an airlaid fibrous article. The fibrous article can be a fibrous web which can be employed to produce an absorbent pad for applications such as disposable diapers, child's training pants, feminine care articles, incontinence articles, and the like.

BACKGROUND OF THE INVENTION

In the general practice of forming fibrous web materials, such as laid fibrous articles, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous web.

The forming surfaces utilized in such systems have been constructed with a wire or screen grid and can typically employ a pneumatic flow mechanism, such as vacuum suction apparatus, to define a differential pressure zone on the forming surface and impose a pressure differential thereon. The pressure difference has typically provided an airflow through the openings or perforations in the screen or grid of the forming surface. The use of vacuum suction to draw the air-entrained fiber stream onto the forming surface, and pass the airflow through the forming surface has been employed in high-speed commercial operations.

The prior practice of forming airlaid fibrous webs has also employed various mechanisms to produce gradations in basis weight along the fibrous webs. For example, the conventional devices have been employed to produce gradations of basis weight along a longitudinal direction of the formed web, i.e., in the direction of movement of the fibrous web through the forming process. Conventional devices have also been employed to provide basis weight variations along a transverse, cross-direction of the formed web.

Conventional vacuum-deposition systems, such as those described above, have continued to exhibit various shortcomings. For example, with the conventional devices, it has been difficult to form airlaid fibrous webs having large changes in basis weight. In particular, the forming surfaces have been constructed to include depressions or pocket regions that have been configured for the formation of the desired high-basis-weights in the formed fibrous web. Where the pocket regions have been large and deep, it has been difficult to direct desired amounts of fiber material into the pocket regions. The conventional techniques have also produced excessively large variations in the distribution of web material along the final, free-surface of the laid fibrous web. As a result, further processing has been required to remove or otherwise redistribute large amounts of the web material. Such redistribution equipment and processes have been difficult to operate and maintain. Accordingly, it would be a substantial advance in the art to provide a method and apparatus which can provide a more reliable and more efficient forming of desired, high-basis-weight regions in an airlaid fibrous web.

BRIEF DESCRIPTION OF THE INVENTION

An apparatus for forming a fibrous web includes a movable, foraminous forming surface and a vacuum-commutator duct system which is located substantially subjacent the forming surface. The vacuum-commutator duct system has an entrance opening that changes in configuration along a longitudinal dimension of the entrance opening.

In a process aspect, a method for forming a fibrous web includes a moving of a foraminous forming surface, and a locating of a vacuum-commutator duct system at a position which is substantially subjacent the forming surface. The vacuum-commutator duct system is configured to have an entrance opening that changes in shape along a longitudinal dimension of the entrance opening.

In a desired aspect, the vacuum-commutator duct system can be substantially stationary. In another aspect, the movable forming surface can include a system of baffles that are arranged to cooperate with the vacuum-commutator duct system.

In its various aspects and features, the present invention can more effectively direct the desired web material directed into appointed, higher-basis-weight sections of the selected forming surface. Additionally, the technique of the invention can better provide a laid web that has less troublesome variations in depth contour along a substantially terminal, free-surface of the formed web. As a result, the desired distributions of web basis weight can be formed with less rearrangement or redistribution of the laid web material. Accordingly, the various features and aspects of the invention can help provide a forming system that can be more effective and reliable, and can operate with less maintenance.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE INVENTION

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Figure 1:
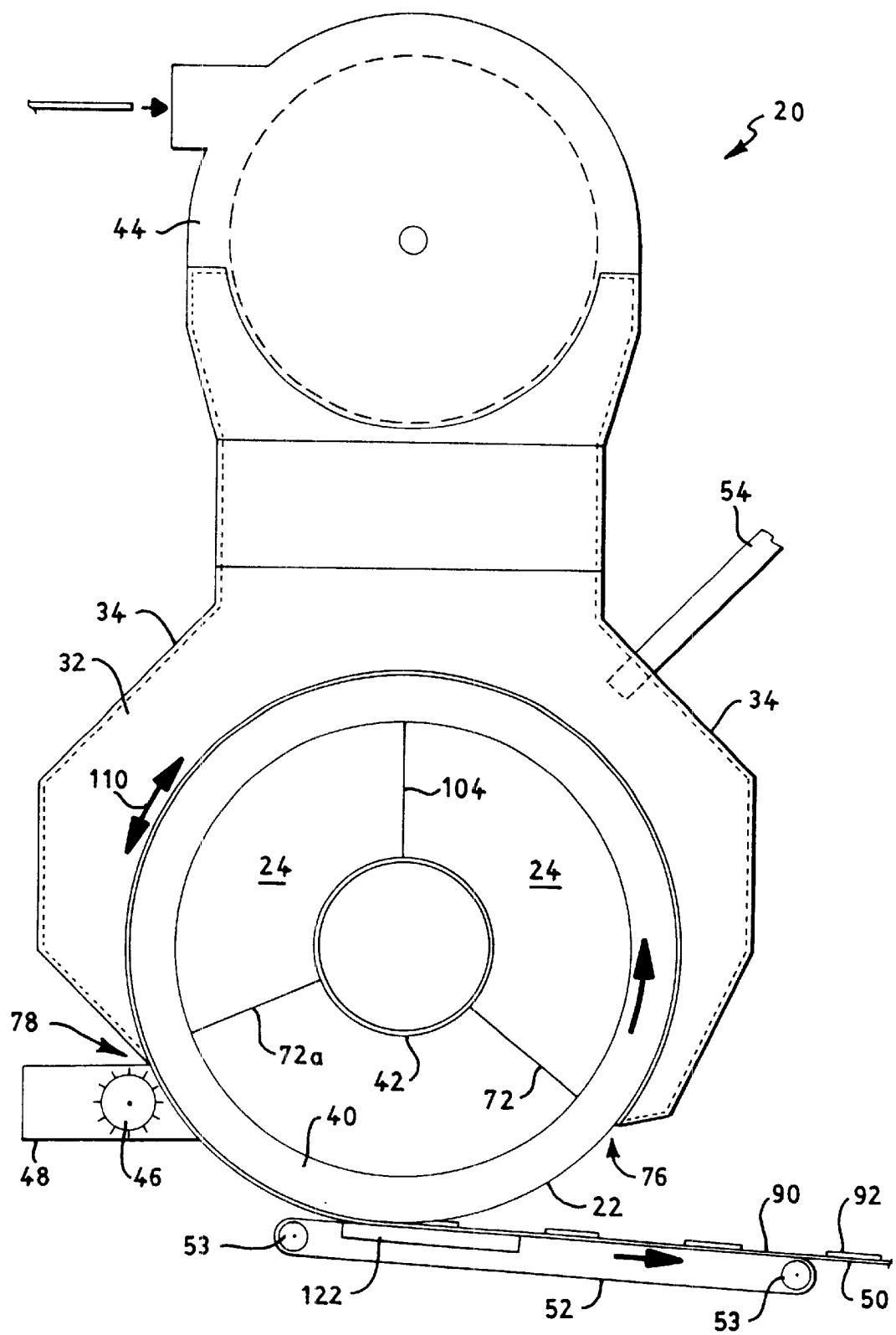
FIG. 1 shows a schematic, side view of a representative method and apparatus that incorporates the present invention.
Figure 2:
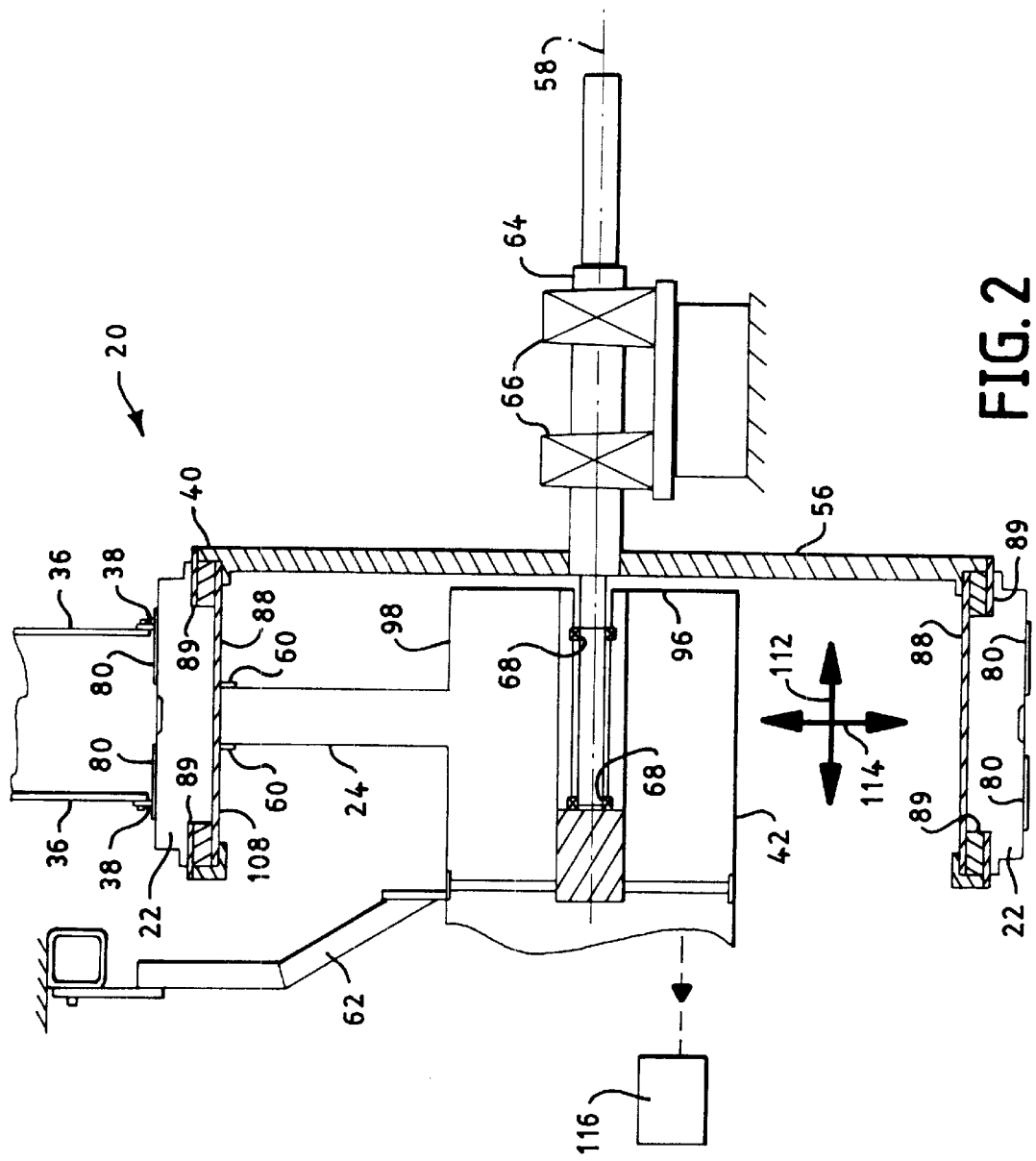
FIG. 2 shows a cross-section through an end view of a portion of a representative method and apparatus having a narrow section of a vacuum commutator duct.

With reference to FIGS. 1 and 2, the process and apparatus of the invention can have a lengthwise, machine-direction 110 which extends longitudinally, a lateral cross-direction 112 which extends transversely, and an appointed z-direction 114. For the purposes of the present disclosure, the machine-direction 110 and is the direction along which a particular component or material is transported lengthwise along and through a particular, local position of the apparatus and method. The cross-direction 112 lies generally within the plane of the material being transported through the process, and is aligned perpendicular to the local machine-direction 110. The z-direction is aligned substantially perpendicular to both the machine-direction 110 and the cross-direction 112, and extends generally along a depthwise, thickness dimension.

Figure 3:
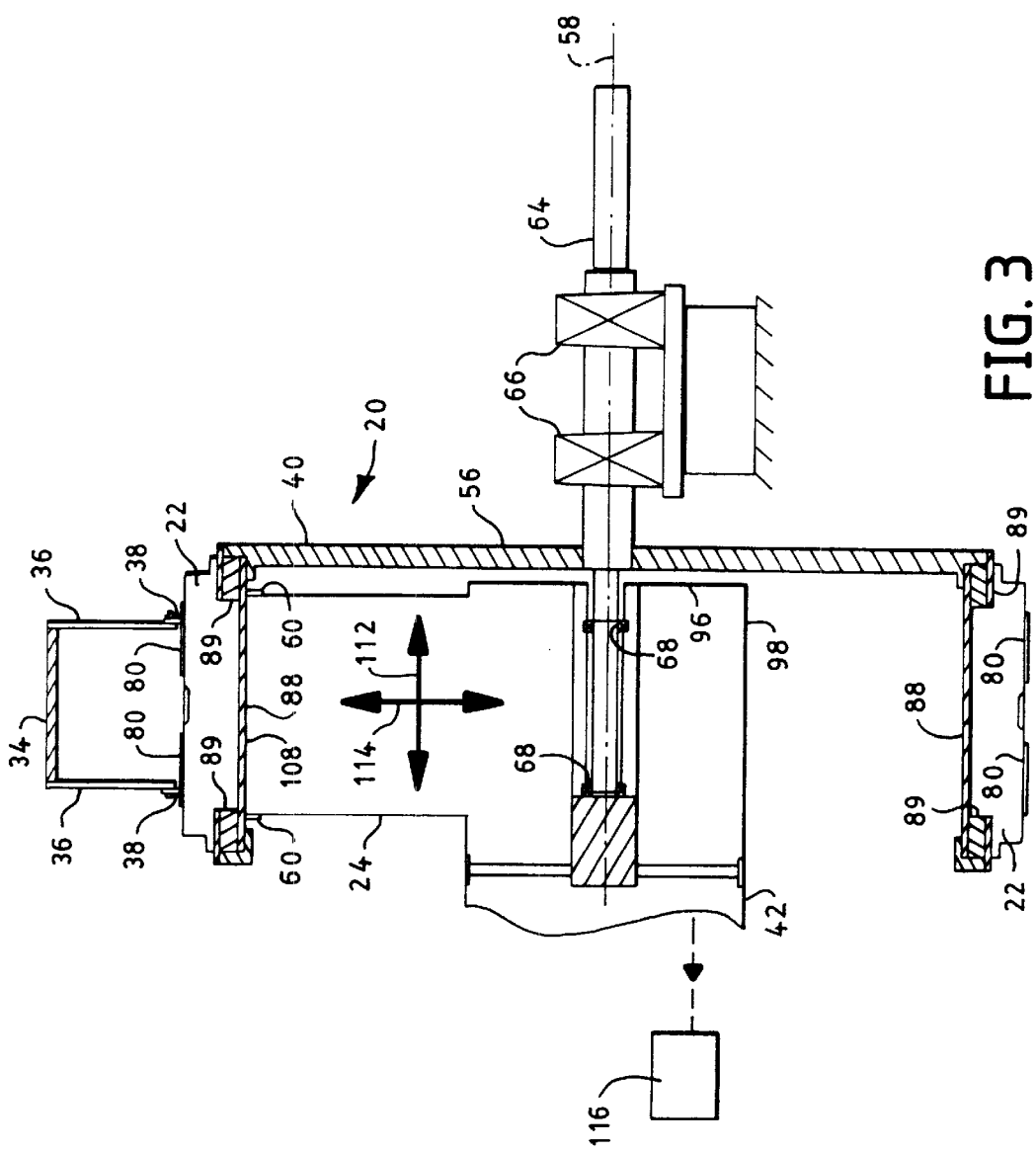
FIG. 3 shows an enlarged, partial cross-section through an end view of a representative method and apparatus having a wider section of the vacuum commutator duct.

With reference to FIGS. 1, 2 and 3, a representative apparatus 20 for forming a fibrous web 50 can include a movable, foraminous forming surface 22, and a vacuum-commutator duct system 24 which is operatively located substantially subjacent the forming surface 22. The vacuum-commutator duct system 24 has an entrance opening 26 that changes in configuration along a longitudinal dimension 30 (e.g. FIG. 4) of the entrance opening 26.

In a process aspect, a method for forming a fibrous web 50 includes a moving of a foraminous forming surface 22, and a locating of a vacuum-commutator duct system 24 at a position which is substantially subjacent the forming surface 22. The vacuum-commutator duct system 24 is configured to have an entrance opening 26 that changes in shape along a longitudinal dimension 30 of the entrance opening 26.

In a particular aspect, the vacuum-commutator duct system 24 can be substantially stationary. In another aspect, the movable forming surface 22 can include a system of baffles that are arranged to cooperate with the vacuum-commutator duct system. In a further aspect, the entrance opening 26 has a lateral width dimension 112, and the lateral width dimension can change when moving along the longitudinal dimension 30 of the entrance opening 26.

By incorporating its various aspects and features, the method and apparatus 20 of the present invention can more effectively direct the desired web material into appointed, higher-basis-weight sections of the foraminous forming surface 22. Such higher-basis-weight sections can, for example, be provided by pocket regions 94 (e.g. FIG. 6). Additionally, the technique of the invention can better provide a laid web 50 that has an exposed, free-surface 118 (e.g. FIG. 10) that can be more readily and efficiently processed to provide a desired surface contour. As a result, the desired distributions of web basis weight can be formed with less rearrangement or redistribution of the laid web material. Accordingly, the various features and aspects of the invention can help provide a forming system that can be more effective and reliable, and can operate with less maintenance.

The fibrous web 50 can have a non-uniform basis weight distribution. In particular, the fibrous web can include a selected arrangement of low-basis-weight regions 90, and relatively high-basis-weight regions 92. To form the desired basis weight distributions in the fibrous web 50, the forming surface 22 can be configured to include the pocket regions 94 or other contours in the forming surface 22 to generate the desired, high-basis-weight regions 92 of the fibrous web 50.

With conventional web forming systems, it has been difficult to satisfactorily fill the appointed, high-basis-weight contour regions of the forming surface 22. The induced airflows through the forming surface 22 have not been adequately controlled to provide the desired concentration of fibrous material within the high-basis-weight regions of the forming surface 22. As a result, there has been an excessively high reliance on a scarfing or other system for redistributing the fibrous material to generate the desired basis weight distributions in the fibrous web 50.

With reference to FIGS. 1, 2 and 3, the method and apparatus of the invention can include a forming chamber 32 through which the forming surface is movable. The forming chamber has an appointed entrance portion 76, and an appointed exit portion 78. A fiber source, such as provided by the fiberizer 44, can be configured to provide fibrous material into the forming chamber 32, and a vacuum generator or other vacuum source 116 can be configured to provide an operative, relatively lower pressure, vacuum condition in the vacuum-commutator duct system 24. As the forming surface 22 enters and then traverses through the forming chamber, the component materials of the fibrous web 50 are operatively carried or transported by an entraining air stream that is drawn through the forming surface 22. Typically, the low pressure, vacuum generating system is constructed and arranged to produce the desired airflow through the forming surface 22. Such vacuum forming systems are well known in the art.

The selected fibrous material may be suitably derived from a batt of cellulosic fibers (e.g., wood pulp fibers) or other source of natural and/or synthetic fibers, which has been disintegrated, in a manner well known in the art, to provide an operative quantity of individual, loose fibers. Accordingly, the method and apparatus can also include a fiberizer 44 which can operatively receive a selected web-forming material, convert the web-forming material into individual fibers, and deliver the fibers into the forming chamber 32. In the illustrated configuration, the fiberizer 44 can be provided by a rotary hammer mill or a rotatable picker roll. Other fiberizers may also be employed, as desired.

Other component materials for producing the fibrous web 50 may also be delivered into the forming chamber 32. For example, particles or fibers of superabsorbent material may be introduced into the forming chamber 32 by employing conventional mechanisms, such as pipes, channels, spreaders, nozzles and the like, as well as combinations thereof. In the representatively shown configuration, the superabsorbent material can be delivered into the forming chamber 32 by employing an operative conduit and nozzle system 54. The illustrated orientation of the delivery conduit 54 is exemplary, and it should be readily appreciated that any operative orientation of the delivery conduit and nozzle system 54 may be employed. The fibers, particles and other desired web material may be entrained in any suitable gaseous medium. Accordingly, any references herein to air as being the entraining medium should be understood to be a general reference which encompasses any other operative entrainment gas. Superabsorbent materials are well known in the art, and are readily available from various suppliers. For example, FAVOR 880 superabsorbent is available from Stockhausen, Inc., a business having offices located in Greensboro, N.C., U.S.A.; and DOW 2035 is available from Dow Chemical Company, a business having offices located in Midland, Mich., U.S.A.

The stream of air-entrained fibers and particles can pass through the forming chamber 32 for deposition onto the selected forming surface 22. The forming chamber can serve to direct and concentrate the air-entrained fibers and particles, and to provide a desired velocity profile in the air-entrained stream of fibers and particles. Typically, the forming chamber is supported by suitable structural members, which together form a support frame for the forming chamber. The frame may be anchored and/or joined to other suitable structural components, as necessary or desirable.

The forming surface 22 can be provided by any suitable mechanism. In the representatively shown configuration, the forming surface 22 is provided by a forming drum 40. Other conventional techniques for providing the forming surface 22 may also be employed. For example, the forming surface 22 may be provided by an endless forming belt. Forming belt systems for producing fibrous webs are well known in the art. Examples of such forming belt systems are available from the Paper Converting Machine Company, a business having offices located in Green Bay, Wis., U.S.A.; and from Curt G. Joa Incorporated, a business having offices located in Sheboygan Falls, Wis., U.S.A.

In the representatively shown configuration, a forming drum system operatively provides the moving forming surface. More particularly, the moving foraminous surface can be provided by an outer peripheral surface region of a rotatable forming drum 40. The forming drum is rotatable in a selected direction of rotation, and can be rotated by employing a drum drive shaft 64 that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction.

The portion of the forming drum which, at a particular point in time, is positioned within the boundaries of the forming chamber 32 can delimit or otherwise provide a lay-down zone of the foraminous forming surface 22. As representatively shown, the vacuum lay-down zone can constitute a circumferential, cylindrical surface portion of the rotatable drum 40. An operative pressure differential is imposed on the surface of the vacuum lay-down zone under the action of a conventional vacuum generating mechanism 116, such as a vacuum pump, an exhaust blower or other suitable mechanism which can provide a relatively lower pressure under the forming surface 22. The vacuum mechanism can operatively withdraw air from the arcuate segment of the forming drum associated with the vacuum lay-down surface through a vacuum supply conduit 42. The foraminous forming surface 22 may include a series of separately removable, forming sections which are distributed circumferentially along the periphery of the forming drum 40. In desired arrangements, the forming sections can provide a selected repeat pattern that is formed in the fibrous web 50. The repeat pattern can correspond to a desired shape of an individual absorbent pad that is intended for assembly or other placement in a desired absorbent article.

Suitable forming drum systems for producing airlaid fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. patent application Ser. No. 09/785,959, now U.S. Pat.

No. 6,330,735, entitled APPARATUS AND PROCESS FOR FORMING A LAID FIBROUS WEB WITH ENHANCED BASIS WEIGHT CAPABILITY by J. T. Hahn et al. which was filed Feb. 16, 2001, the entire disclosure of which is incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

Under the influence of the vacuum generating source 116, a conveying air stream is drawn through the foraminous forming surface 22 into the interior of the forming drum, and is subsequently passed out of the drum through the vacuum supply conduit 42. As the air-entrained fibers and particles impinge on the foraminous forming surface 22, the air component is passed through the forming surface and the fibers-particles component is retained on the forming surface to form a nonwoven fibrous web 50 thereon. Subsequently, with the rotation of the drum, the formed web 50 can be removed from the forming surface. The removal operation may be provided by the weight of the fibrous web 50, by centrifugal force, and by a positive air pressure. The positive air pressure can be produced, for example, by a source of compressed air or a fan which generates a pressurized air flow that exerts a force directed outwardly through the forming surface.

The low-pressure differentials imposed on the foraminous forming surface 22 can be produced by any conventional, vacuum generating mechanism 116, such as an exhaust fan, which is connected to the vacuum supply conduit 42 and is operatively joined to the structure of the forming drum system by employing a conventional coupling mechanism. The interior space of the forming drum 40 can include a high-vacuum forming zone which has the general form of an arcuate segment that is operatively located at the portion of the forming surface 22 that is operatively positioned within the forming chamber 32. In the shown configuration, the high-vacuum forming zone is located generally subjacent the forming chamber, and can include features provided by the vacuum-commutator duct 24.

In a representative operation, the airlaid fibrous web 50 can be formed from the stream of air-entrained fibers (and particles) as the entrainment gas flows the through the openings in the foraminous forming surface 22 and into the rotating forming drum 40. The drum rotation can then pass the airlaid fibrous web 50 from the vacuum lay-down zone to the scarfing zone where excess thickness of the fibrous web can be trimmed and removed to a predetermined extent. As representatively shown, the fibrous web 50 can be operatively processed by a scarfing roll system.

The scarfing system may be positioned at the exit region 78 of the forming chamber 32. The scarfing system can include a scarfing chamber 48 and a scarfing roll 46 which is positioned within the scarfing chamber. The scarfing roll can abrade excess fibrous material from the fibrous web 50, and the removed fibers can be transported away from the scarfing chamber 48 with a suitable discharge conduit, as well known in the art. The removed fibrous material may, for example, be recycled back into the forming chamber 32 or the fiberizer 44, as desired. Additionally, the scarfing roll can rearrange and redistribute the web material along the longitudinal machine-direction of the web and/or along the lateral cross-direction of the web.

The rotatable scarfing roll is operatively connected and joined to a suitable shaft member, and is driven by a suitable drive system (not shown). The drive system may include any conventional apparatus, such as provided by a motor and a coupling, by gear or other transmission mechanism, to the motor or other drive mechanism employed to rotate the forming drum 40. The scarfing roll system can provide a conventional trimming mechanism for removing or redistributing any excess, z-directional thickness of the laid fibrous web that has been deposited on the forming surface 22. The scarfing operation can yield a fibrous web having a selected contour on a major face-surface of the fibrous web that has been contacted by the scarfing roll 46. The surface of the scarfing roll can be adjusted to provide a desired contour along the scarfed surface of the fibrous web 50. In the representatively shown arrangement, the scarfing roll can, for example, be configured to provide a substantially flat surface along the scarfed surface of the fibrous web 50. The scarfing roll can optionally be configured to provide a non-flat surface. The scarfing roll 46 is disposed in spaced adjacent relationship to the forming surface, and the forming surface is translated past the scarfing roll. A conventional transporting mechanism, such as a suction fan (not shown) can draw the removed fibrous material away from the formed fibrous web and out from the scarfing chamber 48.

In the representatively shown configuration, the scarfing roll 46 rotates in a direction which moves a contacting surface of the scarfing roll in a counter-direction that is opposite the movement direction of the laid fibrous web 50. Alternatively, the scarfing roll 46 may be rotated to provide a co-directional movement of the roller surface relative to the surface of the forming drum most proximate thereto. In either situation, the rotational speed of the scarfing roll 46 should be suitably selected to provide an effective scarfing action against the contacted surface of the formed fibrous web. In like manner, any other suitable trimming mechanism may be employed in place of the scarfing roll assembly to provide a cutting or abrading action to the laid fibrous web by a relative movement between the fibrous web 50 and the selected trimming mechanism.

After the scarfing operation, the portion of the forming surface that is carrying the airlaid fibrous web can be moved to an optional pressure blow-off zone of the forming drum system. In the blow-off zone, air can be introduced under pressure and directed radially outwardly against the fibrous web on the portion of the forming surface that becomes aligned with the blow-off zone. The gas pressure can effect a ready release of the fibrous web from the forming surface 22, and the fibrous web 50 can be removed from the forming surface onto a suitable transport mechanism. The web transporter can receive the formed fibrous web 50 from the forming drum 40, and convey the web for further processing. Suitable web transporters can, for example, include conveyer belts, vacuum drums, transport rollers, electromagnetic suspension conveyors, fluid suspension conveyors or the like, as well as combinations thereof. As representatively shown, the web transporter can be provided by a system which includes the illustrated endless conveyor belt 52 disposed about rollers 53. In a particular configuration of the invention, a vacuum suction box 122 can be located below a conveyor belt 52 to help remove the web 50 from the forming surface 22. The vacuum box 122 opens onto the belt 52, and a suction of air out of the vacuum box can draw an air flow through perforations in the conveyor belt. This flow of air can, in turn, operate to draw the web 50 away from the forming surface. The vacuum box can be employed with or without the use of a positive pressure in the blow-off zone. The removed fibrous web can provide an interconnected series of pads, and each pad can have an selected surface contour which substantially matches the contour provided by the various, corresponding portions of the forming surface 22 upon which each individual pad was formed.

With reference to FIGS. 2 and 3, the forming drum 40 has an appointed axis of rotation 58, and is operatively connected and joined to a drive shaft 64 which can rotate the forming drum 40 about the axis of rotation 58. The drive shaft 64 is operatively mounted on a suitable drive shaft support 66. In a desired configuration the drive shaft 64 can extend into the vacuum supply conduit 42, and can be operatively joined to the supply conduit 42 with rotatable support bearings 68 that are mounted in the supply conduit 42. The drive shaft 64 may or may not be configured to be substantially concentric or coaxial with the vacuum supply conduit 42, as desired.

As representatively shown, the vacuum supply conduit can include an end wall 96 and a peripheral wall 98 which delimit the size and shape of the vacuum supply conduit 42. The vacuum supply conduit can have any suitable cross-sectional shape. In the illustrated configuration, the vacuum supply conduit 42 has a generally circular cross-sectional shape. The vacuum supply conduit can be operatively held in position with any suitable support structure, such as a structure which includes the representatively shown, conduit support mount 62. The support mount 62 can also be joined and connected to further components or members that operatively support the portions of the conduit structure that engages the drum drive shaft 64.

With reference to FIGS. 1 through 6, the vacuum commutator duct 24 is operatively connected in fluid communication with the vacuum supply conduit 42. As representatively shown, the vacuum commutator 24 can be operatively joined and connected along an outer peripheral surface of the vacuum supply conduit 42. In the particularly shown configuration, the vacuum commutator duct 24 is connected circumferentially along the outer cylindrical surface of the vacuum supply conduit 42. The vacuum commutator duct 24 can extend generally radially away from the drum axis 58, and alternatively, can extend generally radially away from the vacuum supply conduit 42. Additionally, the vacuum duct 24 can operatively engage a foraminous surface provided by the forming drum 40. The vacuum-commutator duct can include side walls 70, end walls 72 and transition walls 74. The side walls 70 extend radially and circumferentially about the drum drive axis 58 and/or the vacuum supply conduit 42. The end walls 72 can also extend radially and axially with respect to the drum axis 58 and/or the vacuum supply conduit.

Figure 4:
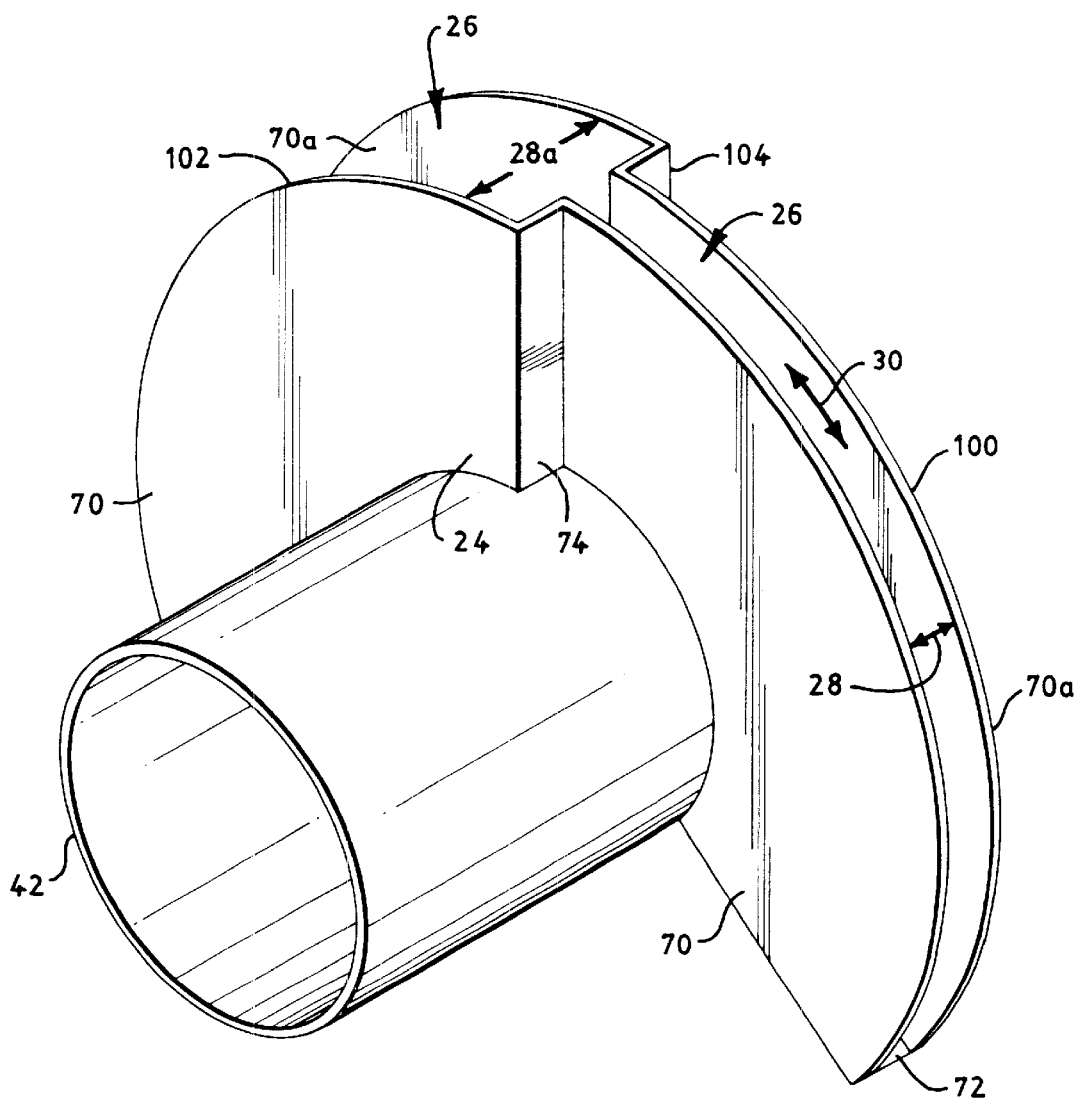
FIG. 4 representatively shows a perspective view of a vacuum-commutator duct that can be employed by the method and apparatus of the invention.
Figure 5:
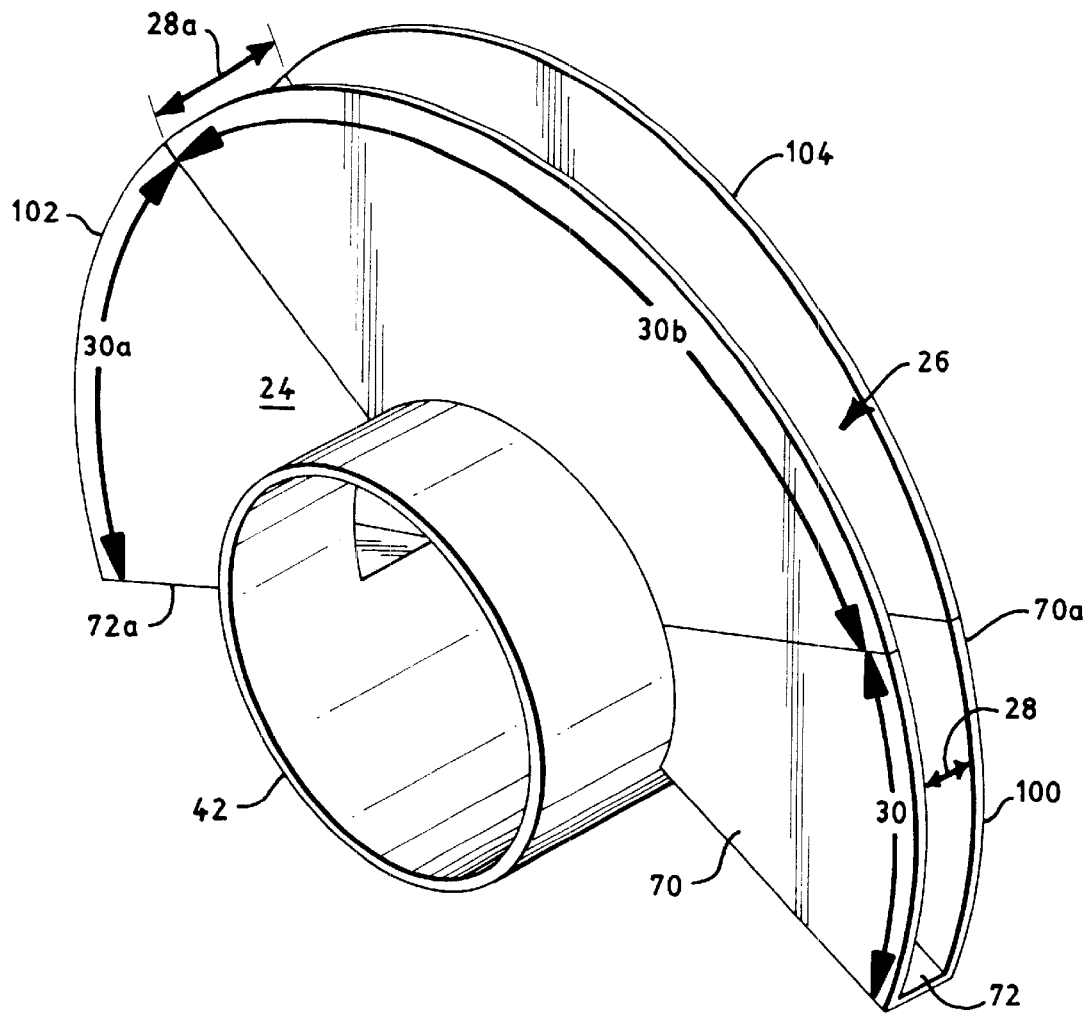
FIG. 5 representatively shows a perspective view of another, tapered vacuum-commutator duct that can be employed by the method and apparatus of the invention.

With reference to FIGS. 4 and 5, the terminal edge portions of the walls of the vacuum-commutator duct 24 can operatively delimit and define the entrance opening 26 of the duct. The entrance region of the vacuum-commutator duct has a first region 100 and at least a second region 102. In a particular feature, the entrance opening 26 of the vacuum-commutator duct system 24 can have a very abrupt change in shape along the longitudinal dimension 30 of the entrance opening 26. In a particular aspect, the entrance opening can have an abrupt change in its width dimension. The change in the shape and width can be substantially step-wise, as representatively shown FIG. 4. In another feature, the entrance opening 26 of the vacuum-commutator duct may include a transition region 104 which is interposed between the first and second regions of the vacuum-commutator duct vacuum-commutator duct system 24. A further feature can include a tapered transition region 104 which provides a gradual change in shape along the longitudinal dimension 30 of the entrance opening 26. As representatively shown in FIG. 5, the tapered transition region can have a selectively graduated change in its width dimension.

With reference to FIGS. 2 and 3, the forming drum 40 can include a circular side wall member 56 which is operatively connected and joined to be rotated by the drum drive shaft 64. As representatively shown, the drum side wall member 56 can be a primary, load-bearing member, and the side wall member can extend generally radially and circumferentially about the drum drive shaft 64.

A drum rim member 88 is operatively connected and joined to the drum side wall member, and is constructed and arranged to provide a substantially free movement of air through the thickness of the rim member. The rim member is generally cylindrical in shape and extends along the direction of the drum axis 58, and circumferentially about the drum axis. As representatively shown, the rim member can be cantilevered away from the drum side wall member 56. The drum rim member 88 has an inward-facing surface 108 which is positioned closely adjacent to the entrance opening 26 of the vacuum-commutator duct 24. To provide an air resistant seal between the rim member 88 and the entrance opening region 26 of the vacuum-commutator duct, rim seals 60 can be operatively positioned and attached along the side wall and end wall members that are employed to form the vacuum-commutator duct 24. The rim seals 60 are configured to allow a relative movement between the drum rim 88 and the entrance opening region 26 of the vacuum-commutator duct, and can be composed of any suitable material. In a particular arrangement, the rim seals 60 can be composed of a wear-resistant, felt material that is arranged to provide a slideable seal.

Figure 6:
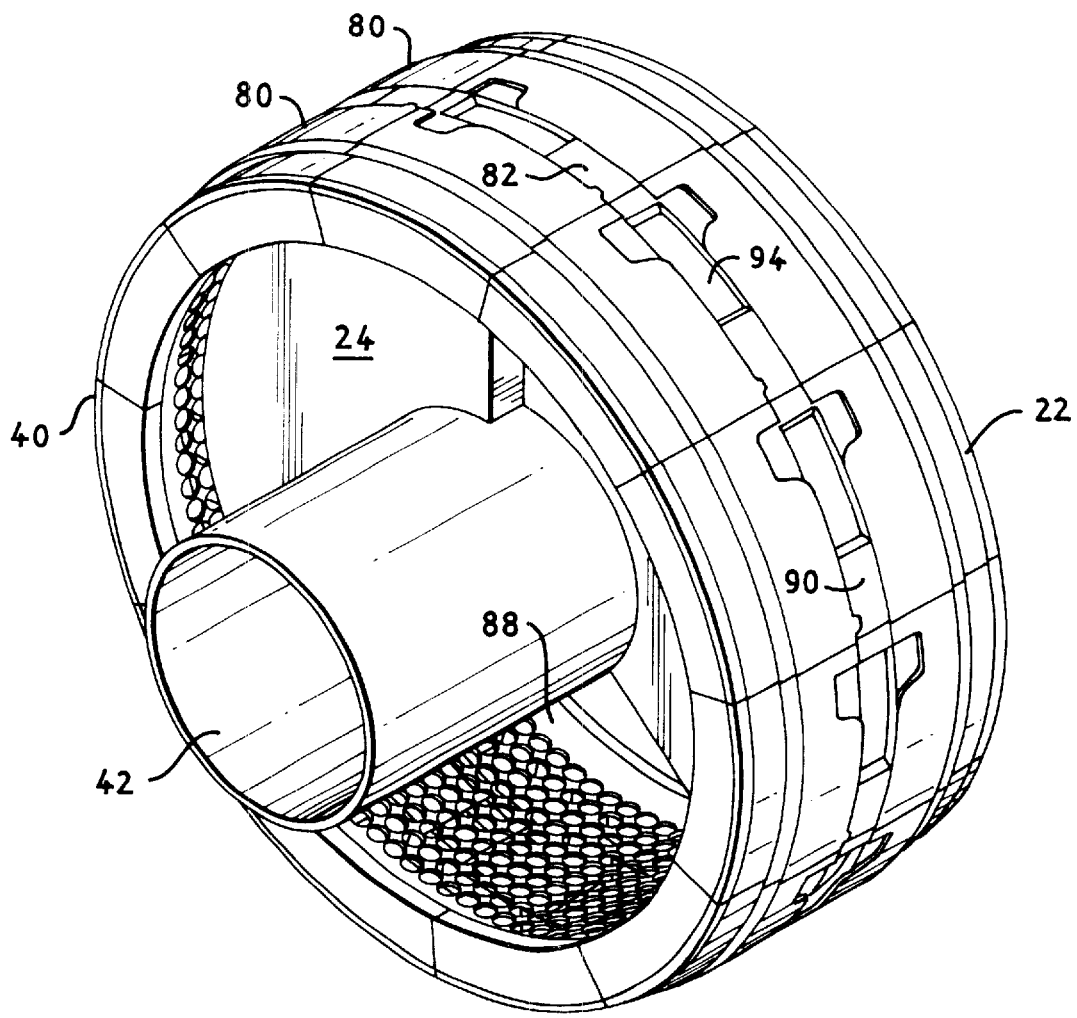
FIG. 6 representatively shows a perspective view of a forming drum with a foraminous forming surface and a vacuum commutator duct.

With reference to FIGS. 2, 3 and 6, the forming surface 22 can be provided along the outer, cylindrical surface of the forming drum 40, and can extend along the axial (cross-directional) and circumferential (machine-directional) dimensions of the forming drum. The structure of the forming surface 22 can be composed of an assembly, and can include a foraminous or otherwise porous member 82 which is operatively connected and joined to the forming drum 40.

The forming surface system can be operatively held and mounted on the drum rim 88 by employing any suitable attachment mechanism. As representatively shown, a system of nuts and bolts can be employed to secure the forming surface 22 onto an operative set of mounting rings, and the mounting rings can be operatively mounted on and secured to the drum rim member 88. In addition to the porous forming member 82, the forming surface 22 can include a plurality of machine-direction baffles 84, and a plurality of cross-direction baffles 86, as representatively shown in FIG. 7. The forming surface assembly can also include a cooperating system of contour rings 80.

Figure 7:
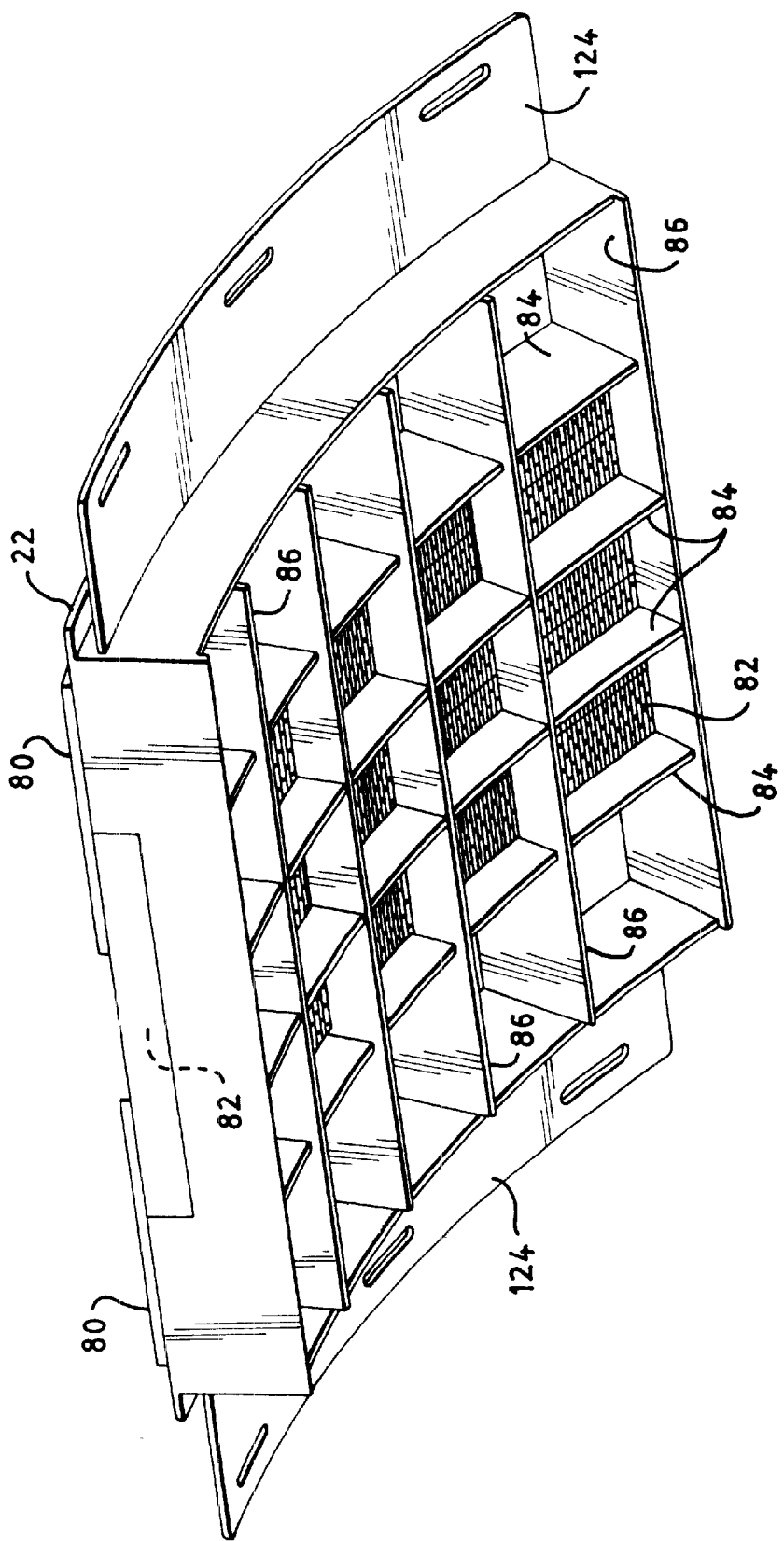
FIG. 7 representatively shows a perspective, bottom view of a portion of a representative forming surface that can be provided on a forming drum.
Figure 8:
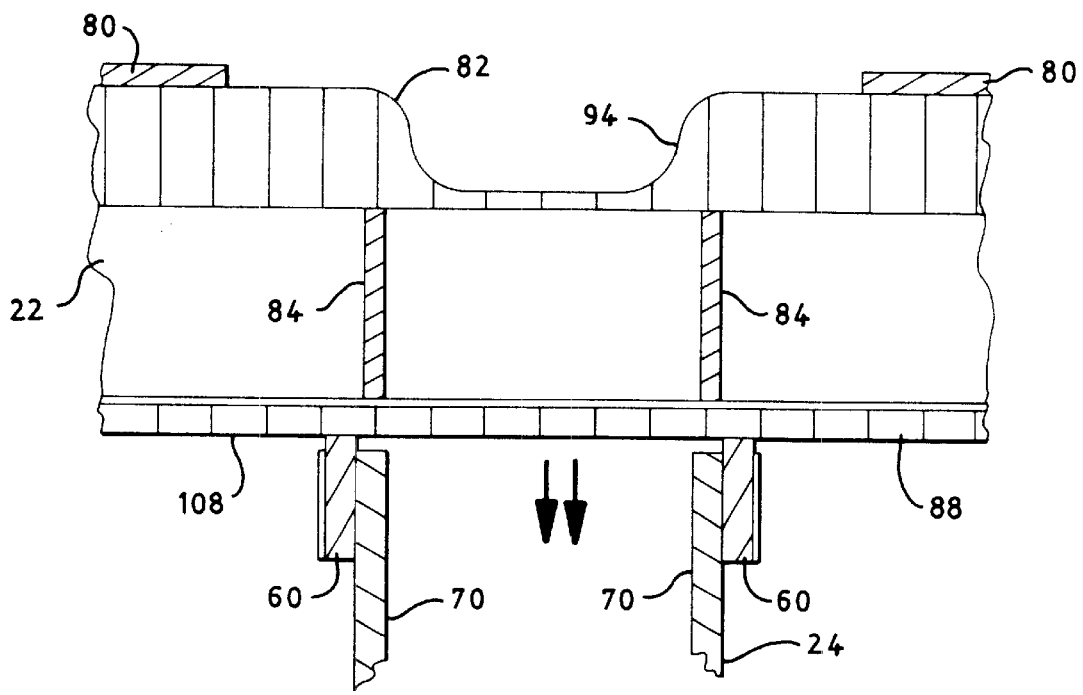
FIG. 8 representatively shows a view of a cross-section at a portion of a forming surface that is positioned at narrow section of the entrance of the vacuum-commutator duct.
Figure 8A:
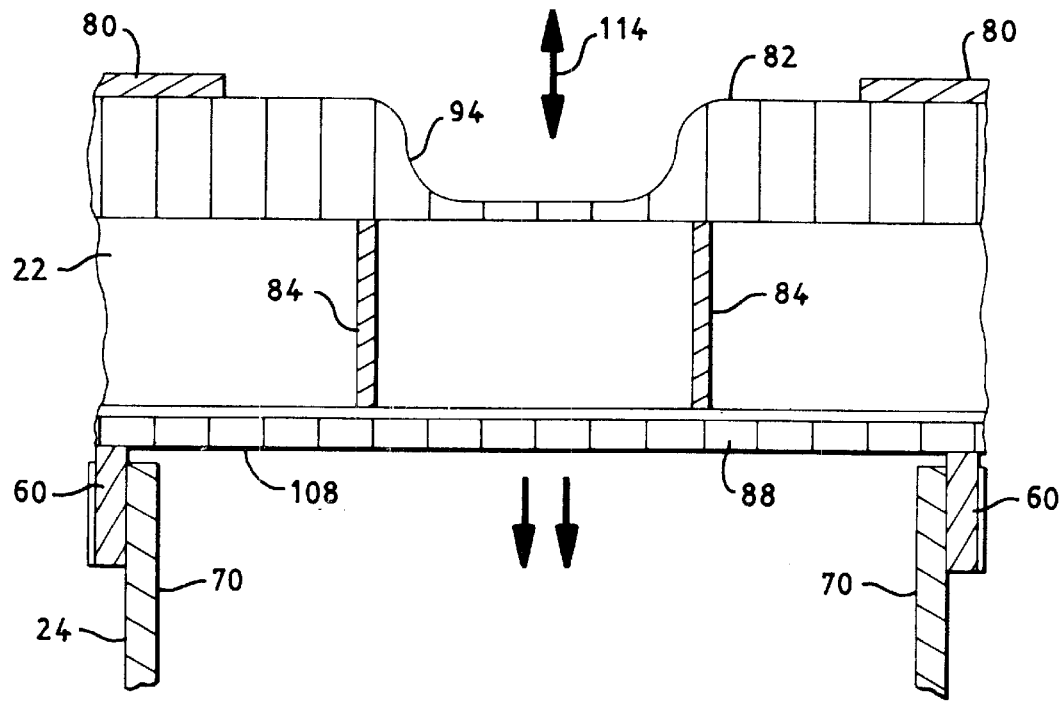
FIG. 8A representatively shows a view of a cross-section at a portion of a forming surface that is positioned at a relatively wide section of the entrance of the vacuum-commutator duct.

With reference to FIGS. 7, 8 and 8A, at least a pair of machine-directional baffles 84 can be operatively positioned and secured subjacent the forming member 82. In a particular aspect the baffles 84 can be located and attached between the porous forming member 82 and the drum rim 88. The baffles 84 can be configured to extend generally radially from the drum axis 58 and can extend circumferentially around the drum axis. Desirably, the baffles 84 can extend along the entire circumference of the forming drum. In a particular aspect of the invention, at least one of the baffles 84 can be positioned laterally adjacent to an appointed, high-basis-weight region of the forming surface 22. In a particular aspect, at least a second circumferentially extending baffle 84 can be laterally spaced from a first circumferentially extending baffle. Accordingly, each of a pair of laterally spaced-apart baffles 84 can be located substantially laterally aligned with, or can be located relatively, laterally-outboard from a corresponding lateral side of the appointed high-basis-weight region of the forming surface 22. The high-basis-weight region can, for example, be provided by the illustrated pocket regions 94. In a further aspect, the machine-direction baffles 84 can be substantially aligned with the side wall members 70 of the vacuum-commutator duct as observed at the first region 100 of the duct entrance opening 26. In particular, the baffles 84 and the wall members 70 can be substantially aligned along the drum axis 58. Additionally, the baffles 84 and the wall members 70 can be substantially aligned along radial dimension of the forming drum 40. Accordingly, the machine-direction baffles 84 can cooperate with the side walls 70 of the vacuum-commutator duct 24 to more effectively direct a flow of air and trained fibers into the pocket regions 94 of the porous forming member 82. The machine-direction baffles can help block undesired, cross-directional air flows under the forming member 82.

The cross-direction baffles 86 can have any operative spacing along the circumferential direction of the forming drum 40. In a desired arrangement, the baffles 86 can be configured to help block undesired, machine-directional air flows in the region under the forming member 82.

The porous forming member 82 can extend along the outer, circumferential periphery of the forming drum 40. The forming member 82 can be composed of any suitable porous material. The foraminous member 82 may include a screen, a wire mesh, a hard-wire cloth, a perforated member or the like, as well as combinations thereof. In a particular aspect, the foraminous member can include a fluted member having open channels which can extend generally radially and can allow a substantially free flow of air or other selected gas from the outward-side of the drum towards the center of the drum. The flutes or channels can have any desired cross-sectional shape, such as circular, oval, hexagonal, pentagonal, other polygonal shape or the like, as well as combinations thereof. The illustrated configuration of the fluted foraminous member can, for example, have a fluted structure in which the channels are arranged to have a rectangular cross-sectional shape. Such honeycomb structures are well known in the art, and can be composed of various materials, such as plastic, metal, ceramics and the like, as well as combinations thereof. For example, suitable materials and structures are available from INNOVENT, a business having offices located in Peabody, Mass., U.S.A.

In a desired feature of the invention, the radially outward surface of the fluted member or other foraminous member 82 can be configured with a selected surface contour. The contoured surface regions of the foraminous member 82 can be formed to have any operative shape. In desired arrangements, the contour shape can be trapezoidal. Alternatively, the contour shape can be domed or flat.

The forming surface 22, and particularly the porous member 82, can include a forming surface contour which is non-uniform along its depth dimension 114. As representatively shown, the forming surface 22 can provide a relatively low-basis-weight region, and at least one relatively high-basis-weight region, such as provided by the pocket regions 94. In a desired configuration, the at least one relatively high-basis-weight region can be positioned along a medial region of the forming surface 22. Alternatively, the at least one relatively high-basis-weight region can be positioned along one or more other, non-medial regions of the forming surface 22.

Accordingly, the forming surface 22 can provide a plurality of concavely contoured forming surface portions that are circumferentially spaced apart along the outer surface of the forming drum. The surface contour can be formed and distributed along the axial and circumferential dimensions of the foraminous member, and can be configured to have a non-constant, contoured depth. In the shown arrangement, the contoured depth can extend radially into or out of the z-directional thickness of the foraminous member 82, and can be configured to provide a desired variation in thickness of the formed fibrous web 50. In desired arrangements, the variation in the z-directional surface contour can have a selected pattern, and the pattern may be regular or irregular in configuration. For example, the pattern of the surface contour can be configured to substantially provide a selected repeat-pattern along the circumferential dimension of the forming drum. The surface contour of the foraminous member 82 can have one or more regions with a first average depth, and can further have one or more regions with a relatively greater second average depth. Each region with the first average depth can provide a lower-basis-weight region of the forming surface, and each region with the greater second depth can provide a relatively higher-basis-weight region of the forming surface. Desirably, each region with the first average depth can be substantially contiguous with an adjacent region with the greater second depth. Each low-basis-weight region of the forming surface can be employed to form a relatively lower-basis-weight portion or section of the fibrous web 50, and each high-basis-weight region of the forming surface can be employed to form a relatively higher-basis-weight portion or section of the fibrous web 50. Subsequently, each lower-basis-weight section of the fibrous web can be employed to form a relatively lower-basis-weight section of an individual fibrous pad 50, and each higher-basis-weight section of the fibrous web can be employed to form a relatively lower-basis-weight section of such individual fibrous pad 50.

The forming member 82 can include a plurality of longitudinally spaced-apart pocket regions 94. As representatively shown, the pocket regions can have a selected serial arrangement along the circumferential direction of the forming drum 40. The pocket regions 94 can provide sections of the forming member 82 that are appointed for forming the desired, high-basis-weight regions 92 (e.g. FIG. 1) of the fibrous web 50. Accordingly, the pocket regions 94 can provide selected high-basis-weight regions of the forming member 82.

As representatively shown, cooperating non-pocket regions of the forming member 82 can be interposed between the pocket regions 94, and can be appointed for the formation of the desired low-basis-weight regions 90 of the fibrous web 50. Accordingly, the non-pocket regions of the forming member 82 can provide appointed, low-basis-weight regions of the forming member 82.

In a further aspect, one or more non-flow regions of the forming drum surface may be operatively formed by employing any suitable blocking mechanism that can cover or otherwise occlude the z-directional flow of gas through selected regions of the forming surface. As a result, the blocking mechanism can deflect or reduce the amount of fibers deposited on the areas of the forming surface that are covered by the blocking mechanism. The blocking mechanism can optionally be configured to form other desired elements, such as a series of key notches, on the laid fibrous web 50. The key notches can, for example, provide sensing point for locating and positioning a subsequent severing of the longitudinally extending fibrous web into discrete fibrous pads 50.

With reference to FIGS. 6 and 7, at least one side-masking member, such as provided by a side contour ring 80 can be disposed on the foraminous member 82. Desirably, the invention can include a cooperating system side-masking members. As representatively shown, a pair of laterally opposed, side contour ring members 80 can be configured to extend circumferentially around the forming drum 40. In a particular aspect, the contour rings 80 can be operatively attached and positioned along laterally opposed, outboard edge regions of the foraminous member 82. As representatively shown, the contour rings 80 can be joined and assembled to the forming surface 22 by employing conventional attaching or mounting mechanisms. Additionally, the assembly can include side flanges 124 which can provide suitable mounting members for operatively securing the forming surface assembly to the circumferential periphery of the forming drum 40.

In desired arrangements, the contour ring members can be selectively shaped and contoured, and can be configured to provide cooperating, symmetrically opposed contour rings. Each of the contour rings can have a cross-directional extent that is varied in a selected pattern to provide a laterally varying, inboard side-edge contour. In particular arrangements the side contours in the first and second ring members can be substantial mirror-images of each other. In another feature, at least one ring member, can include one or more key tabs. The individual key tabs may, for example, be employed for marking or otherwise identifying each intended article length along the circumference of the forming drum. Such contour rings can be particularly advantageous when the forming drum system is employed to produce absorbent pads for use in disposable, shaped absorbent articles, such as diapers, children's training pants, feminine care products, adult incontinence products and the like. The contour rings or other side-masking members can be configured to substantially prevent a deposition of fibers in selected regions along the side margins of the forming surface 22 to thereby hell) to form corresponding arcuate, cut-out sections along the side regions of the laid fibrous web 50.

In desired arrangements, the inboard side edges of the ring members 80 can be contoured along the cross-direction 112. In the representatively shown arrangement, the side walls of the contoured ring members can have a serpentine, undulating contour along the cross-direction 112. Additionally, the first and second contour rings 80 and can be cooperatively arranged and configured to provide alternating, narrow and wide regions of the forming member 82 that are exposed to the depositing web material. Accordingly, the side contour rings 80 can help provide the desired shapes along the lateral side edges of the fibrous web 50. As representatively shown, the inboard edge contours of the side contour rings 80 can be substantially mirror images of each other. The inboard side edges of the contour rings 80 can optionally have a substantially straight configuration along the machine-direction 110 to produce a substantially rectangular, ribbon shaped region of the forming member 82 that is exposed to the depositing web material.

With reference to FIGS. 1, 2 and 3, the forming chamber 32 can include side wall members 36, and a system of cover wall members 34. As representatively shown, the forming surface 22 can be operatively moved through the forming chamber 32 by moving the forming member 82 past and closely adjacent to the bottom terminal edges of the forming chamber side wall members 36. In a desired configuration, chamber seals 38 can be operatively positioned and arranged along the terminal edges of the chamber side wall members 36. The chamber seals 38 extend along the entire machine-directional length of the chamber side wall members 36. The chamber seals 38 are configured to provide an effective blocking of undesired air flows into the forming chamber 32 past the bottom, terminal edges of the chamber side wall members 36. The chamber seals 38 can operatively engage an outward-facing, substantially non-porous portion of the forming surface 22 while allowing a substantially free, relative movement between the forming surface 22 and the forming chamber 32. The substantially non-porous portion of the forming surface 22 can, for example, be provided by an outward surface of the contour rings 80 or the outward surface of another surface member that extends circumferentially along the periphery of the forming drum. The chamber seals may be composed of any operative material. In a desired arrangement, the chamber seals 38 can be composed of nylon and configured to provide a sealing member that slideably engages the selected portions of the forming surface.

The vacuum-commutator duct system 24 can include a first end wall member 72, and at least a second end wall member 72a which is longitudinally spaced from the first end wall member. A first side wall member 70 can interconnect between the first and second end wall members, and at least a second side wall member 70a can interconnect between the first and second end wall members, and can be laterally spaced from the first side wall member 70. To provided a desired cooperation with the forming drum rim 88, an entrance region of the first side wall member 70 can have a circumferentially arcuate edge region, and an entrance region of the second side wall member 70a can have a similar, circumferentially arcuate edge region. The first and second end wall members 72 of the vacuum-commutator duct system 24 can be operatively attached to the vacuum supply conduit member 42. Additionally, the first and second side wall members 70 can be operatively attached to the vacuum supply conduit. As representatively shown, the vacuum supply conduit 42 can be configured to extend axially along a rotational axis 58 of the forming drum 40.

With reference to FIGS. 4 and 5, the entrance opening 26 of the vacuum-commutator duct system 24 can have a first opening section 100 with a first lateral width 28, and at least a second opening section 102 with a second lateral width 28a. The second lateral width can differ from the first lateral width, and in a particular feature, the first lateral width of the entrance opening 26 can be configured to operatively match a lateral width of the relatively high-basis-weight region of the forming surface 22. As representatively shown, the first lateral width of entrance opening 26 can be smaller and narrower than the second lateral width. Additionally, the second lateral width 28a can be configured to be substantially equal to or greater than a desired maximum lateral width of the web 50. In a particular aspect, the second lateral width 28a can be configured to be substantially equal to or greater than a desired maximum lateral width of the relatively low-basis-weight, intermediate regions of the web that are interposed between successive high-basis-weight regions of the web 50 along its longitudinal, machine-direction.

In another feature, the first opening section 100 can have a first lateral width 28 which is substantially constant along a first longitudinal extent thereof. Additionally, the second opening section 102 can have a different, second lateral width 28a which is substantially constant along a second longitudinal extent 30a thereof. In a further feature, the entrance opening 26 can include a generally tapered, transition section 104 that is positioned between the first and second opening sections 100 and 102, respectively, and extends along a transition length 30b. The non-abrupt, gradual change in width provided by the transition section 104 can help to better provide the desired distributions of web material across the forming member 82 and across the forming surface 22.

The first longitudinal length 30 of the first opening section 100 can be at least a minimum of about 10% of the path length along which the formation of the web 50 occurs while operatively moving through the forming chamber 32 from the chamber entrance 76 to the chamber exit 78. The first longitudinal length 30 can alternatively be at least about 15%, and optionally, can be at least about 25% of the operative path length of the web 50 through the forming chamber 32 to provide improved performance. In other aspects, the first longitudinal length 30 can be up to a maximum of about 75%, or more, of the operative path length of the web 50 through the forming chamber 32. The first longitudinal length 30 can alternatively be up to about 65%, and optionally, can be up to about 50% of the path length of the web 50 through the forming chamber 32 to provide improved effectiveness.

The described configurations of the first longitudinal length 30 can provide an improved filling of the pocket regions 94 or other high-basis-weight regions of the forming surface. If the first longitudinal length 30 is outside the selected values, insufficient amounts of airflow may be delivered to the beginning region of the fiber deposition process, and the pocket regions 94 may be incompletely filled. Additionally, an excessive amount of recycle mass flow may be generated at the scarfing operation, and an excessive weight variability may be produced in the formed, fibrous web.

The second longitudinal length 30a of the first opening section 102 can be at least a minimum of about 25% of the path length along which the formation of the web 50 occurs while operatively moving through the forming chamber 32 from the chamber entrance 76 to the chamber exit 78. The second longitudinal length 30a can alternatively be at least about 35%, and optionally, can be at least about 50% of the operative forming path length through the forming chamber 32 to provide improved performance. In other aspects, the second longitudinal length 30a can be up to a maximum of about 90%, or more, of the operative forming path length through the forming chamber 32. The second longitudinal length 30a can alternatively be up to about 85%, and optionally, can be up to about 75% of the operative forming path length through the forming chamber to provide improved effectiveness.

The described configurations of the second longitudinal length 30a can provide an improved filling of the desired low-basis-weight regions and high-basis-weight regions of the forming surface. If the second longitudinal length 30a is outside the selected values, insufficient amounts of airflow may be delivered to the end regions of the fiber deposition process. The pocket regions 94 may be incompletely filled, and any low-basis-weight regions that are positioned laterally outboard of the pocket regions may be incompletely filled. Additionally, an excessive amount of recycle mass flow may be generated at the scarfing operation, and an excessive weight variability may be produced in the formed, fibrous web.

Where the method and apparatus includes the vacuum-commutator duct having an abrupt change in shape, the longitudinal length of the transition region 104 can be substantially zero. Where the vacuum-commutator duct has the tapered transition region, the transition region can have a discrete, longitudinal transition length 30b. The transition length 30b can be at least a minimum of about 1% of the path length along which the formation of the web 50 occurs while operatively moving through the forming chamber 32 from the chamber entrance 76 to the chamber exit 78. The transition length 30b can alternatively be at least about 7%, and optionally, can be at least about 10% of the operative forming path length through the forming chamber 32 to provide desired performance. In other aspects, the transition length 30b can be up to a maximum of about 50%, or more, of the path length along which the formation of the web 50 occurs while operatively moving through the forming chamber 32 from the chamber entrance 76 to the chamber exit 78. The transition length 30b can alternatively be up to about 33%, and optionally, can be up to about 25% of the operative forming path length through the forming chamber 32 to provide desired effectiveness.

The described configurations of the tapered transition region can help provide an improved filling of the desired low-basis-weight regions and high-basis-weight regions of the forming surface. If the longitudinal transition length 30b is outside the selected values, the operation of the first and second opening sections of the vacuum-commutator duct may be excessively compromised. Additionally, there may be an excessive amount of airflow leakage between the vacuum-commutator duct and the forming surface if the longitudinal transition length 30b is too large.

Figure 9:
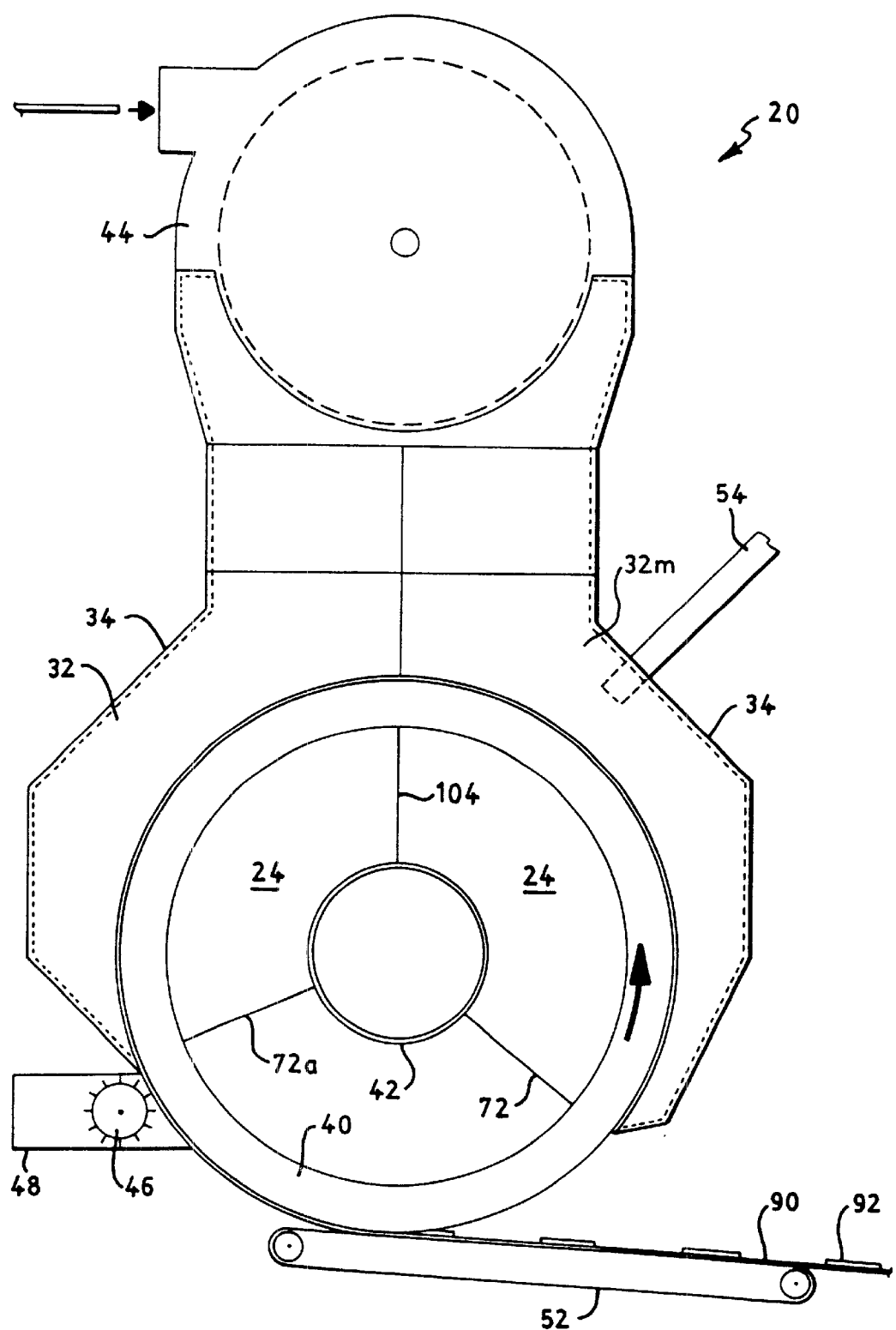
FIG. 9 representatively shows a schematic, side view of a representative method and apparatus that incorporates a forming chamber that includes a selectively varied shape that changes to approximately match the entrance shape of the vacuum-commutator duct.
Figure 10:
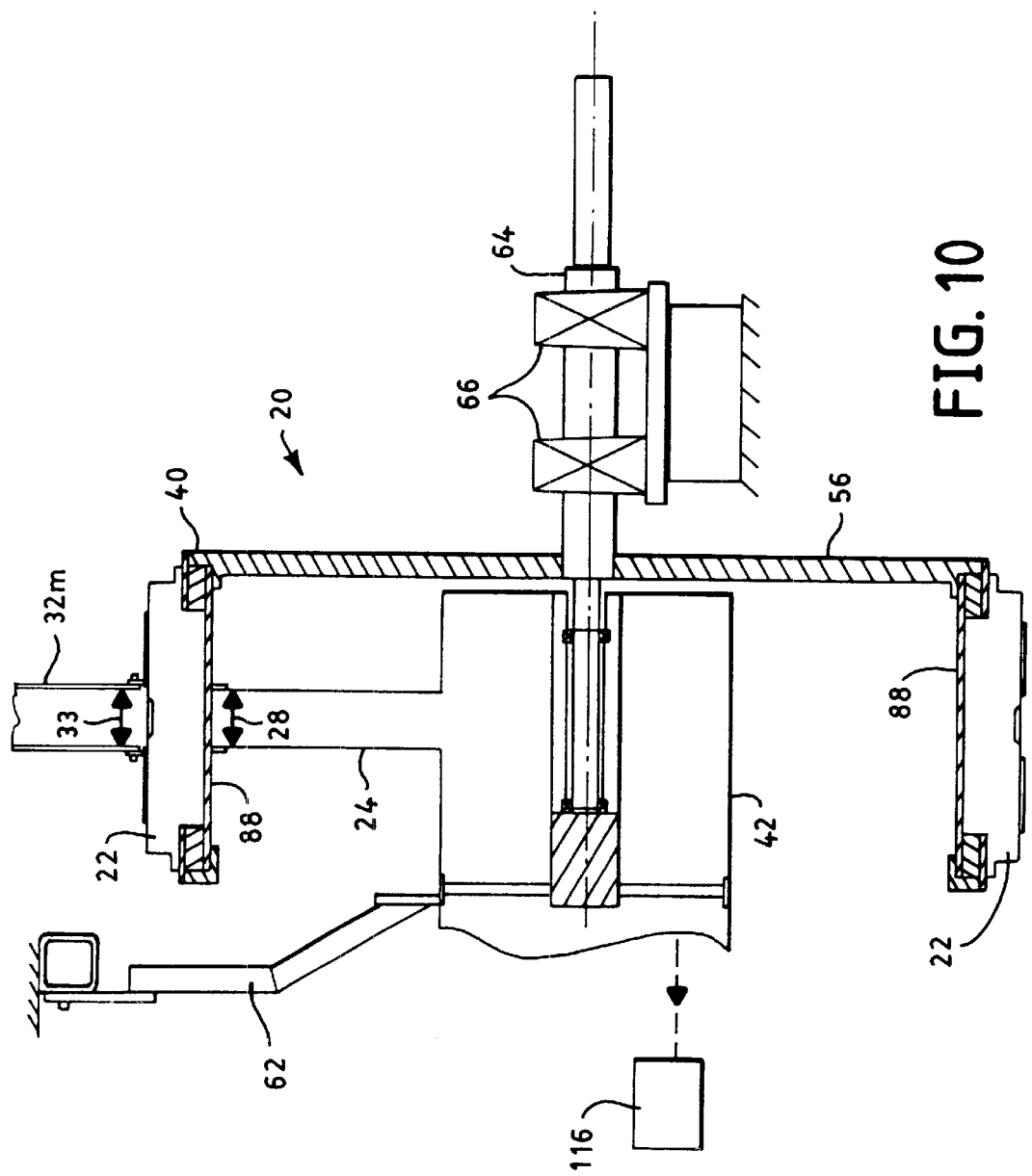
FIG. 10 shows a cross-section through an end view of a portion of a representative method and apparatus having a narrow section of a vacuum commutator duct and a correspondingly narrowed forming chamber.

With reference to FIGS. 9 and 10, another feature of the method and apparatus can incorporate a forming chamber 32 that includes a selectively varied shape. In a particular aspect, the shape of a selected, machine-directional portion 32m of the forming chamber can be modified and varied in at least the regions of the forming chamber that are located proximate the forming surface 22 of the forming drum 40. The shape of the modified forming chamber portion 32m can be cooperatively varied and changed to approximately match the changing shape of the correspondingly aligned portions of the entrance opening of the vacuum-commutator duct. In a desired aspect, the cross-directional width dimension 33 of the forming chamber (at least in the region of the forming chamber that is proximate the forming surface 22) can be cooperatively modified and changed to approximately match the entrance width 28 of the correspondingly positioned or aligned portions of the vacuum-commutator duct 24. In particular arrangements, the cross-directional width dimension of the forming chamber (in at least the region of the forming chamber that is proximate the forming surface) can be cooperatively modified and changed to be substantially equal to or slightly greater than the entrance width 28 of the corresponding portions of the vacuum-commutator duct 24.

Accordingly, in the region of the vacuum-commutator duct having a narrow-width entrance opening, the proximately positioned portion of the forming chamber can have a corresponding, narrow chamber width. In the region of the vacuum-commutator duct having a wider-width entrance opening, the proximately positioned portion of the forming chamber can have a corresponding, wider chamber width. Where the vacuum-commutator duct has an entrance opening that tapers in width, the proximately positioned portions of the forming chamber can correspondingly taper in width. Where the vacuum-commutator duct has an entrance opening that abruptly changes in width, the proximately positioned portions of the forming chamber can correspondingly, abruptly change in width.

The cooperating, approximately matched shapes and dimensions of the forming chamber and the vacuum-commutator duct can help to reduce excessive turbulence in the forming chamber, particularly in the chamber regions that are generally proximate the forming surface 22. As a result, the cooperating, approximately matched shapes and dimensions can help to more effectively direct the air entrained materials to desired locations on the forming surface.

It will be readily apparent that various conventional devices and techniques can be employed to further process the web 50. For example, various conventional devices and techniques can be employed to sever fibrous web 50 into predetermined lengths to provide selected laid fibrous articles. The severing system may, for example, include a die cutter, a water cutter, a rotary knives, reciprocating knives, energy beam cutters, particle beam cutters or the like, as well as combinations thereof. After severing, the discrete fibrous pads 50 can be transported and delivered for further processing operations, as desired.

Figure 11:
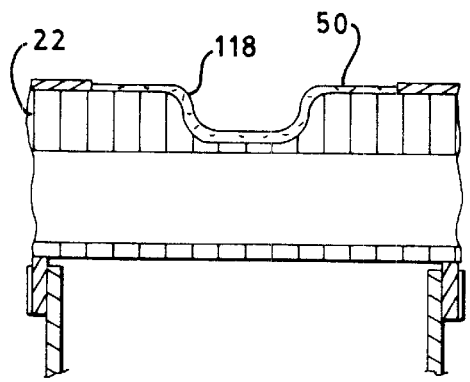
FIG. 11 representatively shows a cross-section through an end view of a portion of a forming surface on which a formation of the selected web has been partially completed in a high-basis-weight, pocket region of the forming surface while employing a conventional forming system.
Figure 11A:
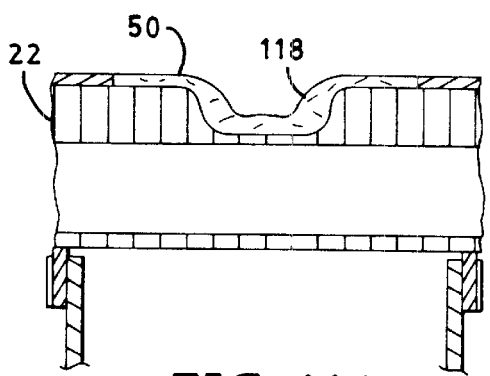
FIG. 11A representatively shows a cross-section through an end view of a portion of the forming surface on which the formation of the selected web has been approximately 50% completed in the pocket region of the forming surface while employing the conventional forming system.
Figure 11B:
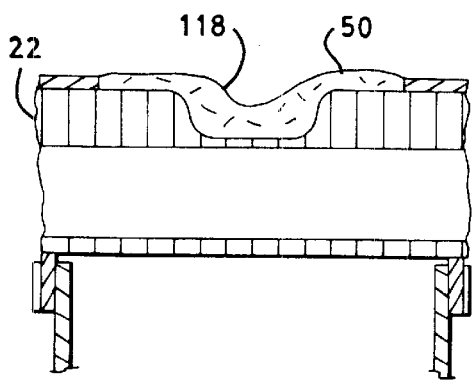
FIG. 11B representatively shows a cross-section through an end view of a portion of the forming surface on which the formation of the selected web has been further completed in the pocket region of the forming surface while employing the conventional forming system.
Figure 11C:
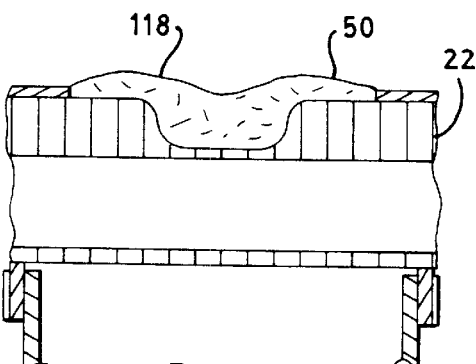
FIG. 11C representatively shows a cross-section through an end view of a portion of the forming surface on which the formation of the selected web has been substantially completed while employing the conventional forming system.
Figure 11D:
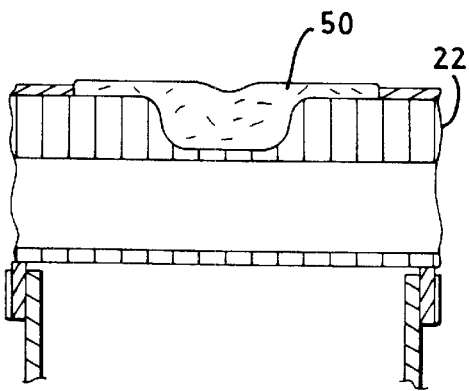
FIG. 11D representatively shows a cross-section through an end view of a portion of the forming surface with the web that has been formed with the conventional forming system, wherein the formed web has been subjected to a subsequent scarfing operation.

FIGS. 11 through 11D show a representative sequence during which the web material is accumulated onto a forming surface while employing a conventional forming system. In FIGS. 11 through 11C, the shown portion of the web has traversed through approximately 25%, 50%, 75% and 100%, respectively, of the path length along which the formation of the airlaid web occurs while the forming surface is moving through the forming chamber. In FIG. 11D, the shown portion of the web has been scarfed by the scarfing roll. The illustrated sequence representatively shows the difficulty in adequately filling the high-basis-weight, pocket regions of the forming surface. Even after the web has been subjected to a scarfing operation, the pocket regions may remain incompletely filled, and the desired basis weight distributions of web material may not be provided.

Figure 12:
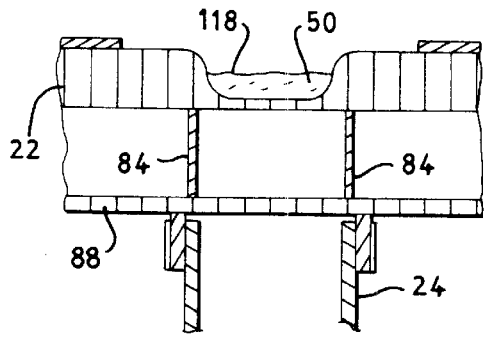
FIG. 12 representatively shows a cross-section through an end view of a portion of a forming surface on which a formation of the selected web has been approximately 50% completed in a high-basis-weight, pocket region of the forming surface while employing the forming system of the invention.
Figure 12A:
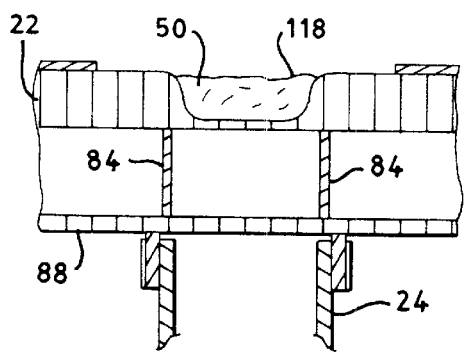
FIG. 12A representatively shows a cross-section through an end view of a portion of the forming surface on which the formation of the selected web has been further completed in the pocket region of the forming surface while employing the forming system of the invention.
Figure 12B:
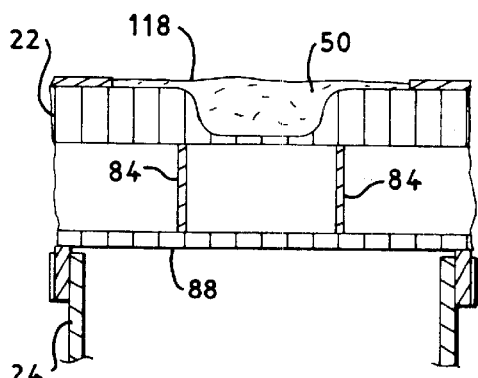
FIG. 12B representatively shows a cross-section through an end view of a portion of the forming surface on which the formation of the selected web has been partially completed in relatively low basis weight, side regions of the forming surface while employing the forming system of the invention.
Figure 12C:
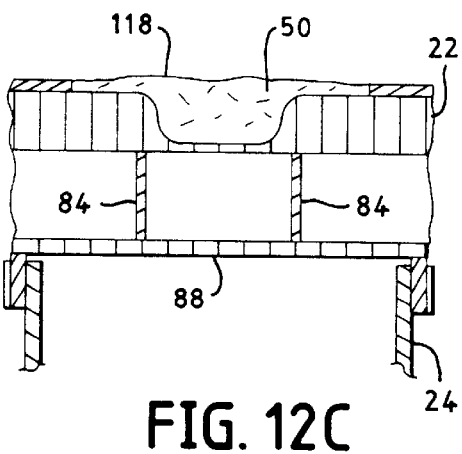
FIG. 12C representatively shows a cross-section through an end view of a portion of the forming surface on which the formation of the selected web has been substantially completed while employing the forming system of the invention.
Figure 12D:
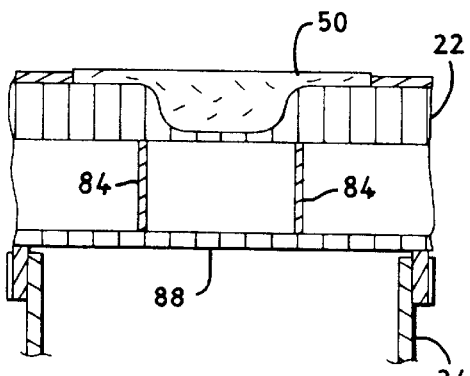
FIG. 12D representatively shows a cross-section through an end view of a portion of the forming surface with the web that has been formed with the forming system of the present invention, wherein the formed web has been subjected to a subsequent scarfing operation.

FIGS. 12 through 12D show a representative sequence over which the web material can be accumulated onto a forming surface while employing the method and apparatus of the present invention. In FIGS. 12 through 12C, the shown portion of the web has traversed through approximately 25%, 50%, 75% and 100%, respectively, of the path length along which the formation of the web 50 occurs while operatively moving through the forming chamber 32 from the chamber entrance 76 to the chamber exit 78. As representatively shown, the path length can correspond to the effective, machine-directional length of the lay-down zone provided by the method and apparatus of the invention. In FIG. 12D, the shown portion of the web has been scarfed by the scarfing roll. The illustrated sequence schematically shows an improved ability to fill the high-basis-weight, pocket regions of the forming surface, and an improved ability to provide the desired basis weight distributions of web material, as compared to the conventional system.

In the various attachments and securements that may be needed for the construction of the method and apparatus of the invention, it should be readily apparent that any conventional attachment or securement technique may be employed. Such techniques may, for example, include adhesives, welds, screws, bolts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metallic composites, ceramic composites, and the like, as well as combinations thereof. The materials are typically selected to provide desired levels of strength, durability, ease of manufacture, and ease of maintenance.

Although various illustrative and representative configurations have been described in detail herein, it is to be appreciated that other variants, modifications arid arrangements are possible. All of such variations, modifications and arrangements are to be considered as being within the scope of the present invention.

What is claimed is:

1. An apparatus for forming a fibrous web, comprising:
    a movable, foraminous forming surface; and
    a vacuum-commutator duct system which is located substantially subjacent said forming surface; wherein
        said vacuum-commutator duct system has an entrance opening that changes in configuration along a longitudinal dimension of said entrance opening.

2. An apparatus as recited in claim 1, wherein said vacuum-commutator duct system is substantially stationary.

3. An apparatus as recited in claim 1, wherein said entrance opening has a lateral width dimension, and said lateral width dimension changes when moving along said longitudinal dimension of said entrance opening.

4. An apparatus as recited in claim 1, wherein said entrance opening of said vacuum-commutator duct system has a substantially step-wise change in shape along said longitudinal dimension of said entrance opening.

5. An apparatus as recited in claim 1, wherein said entrance opening of said vacuum-commutator duct system has a tapered change in shape along said longitudinal dimension of said entrance opening.

6. An apparatus as recited in claim 1, wherein said forming surface includes a relatively low-basis-weight region, and at least one relatively high-basis-weight region.

7. An apparatus as recited in claim 6, wherein said at least one relatively high-basis-weight region is positioned along a medial region of said forming surface.

8. An apparatus as recited in claim 6, wherein
    said entrance opening of the vacuum-commutator duct system has a first opening section with a first lateral width, and at least a second opening section with a second lateral width;
    said second lateral width differs from said first lateral width; and
    said first lateral width of the entrance opening operatively matches a lateral width of said relatively high-basis-weight region of the forming surface.

9. An apparatus as recited in claim 8, wherein
    said forming surface includes
        a foraminous forming member;
        a first circumferentially extending baffle; and
        at least a second circumferentially extending baffle that is laterally spaced from said first circumferentially extending baffle;
    said first and second circumferential baffles are positioned subjacent said foraminous forming member;
    said first and second circumferentially extending baffles are positioned laterally adjacent said relatively high-basis-weight region of the forming surface;
    said vacuum-commutator duct system includes side wall members; and
    said first and second circumferentially extending baffles are substantially aligned with said side wall members of said vacuum-commutator duct system, as observed at said first opening section of the vacuum-commutator duct system.

10. An apparatus as recited in claim 6, wherein said entrance opening of the vacuum-commutator duct system has a first opening section with a first longitudinal extent that has a substantially constant, first lateral width, and at least a second opening section with a second longitudinal extent that has a substantially constant, second lateral width;

said second lateral width differs from said first lateral width; and said first lateral width of the entrance opening operatively matches a lateral width of said relatively high-basis-weight region of the forming surface.

11. An apparatus as recited in claim 6, wherein said entrance opening of the vacuum-commutator duct system includes:

a first opening section having a first longitudinal extent with a substantially constant, first lateral width;

at least a second opening section having a second longitudinal extent with a substantially constant, second lateral width which differs from said first lateral width; and and a substantially tapered, transition section positioned between said first and second opening sections.

12. An apparatus as recited in claim 1, wherein said forming surface includes a relatively low-basis-weight region, and at least one relatively high-basis-weight, pocket region.

13. An apparatus as recited in claim 1, wherein said forming surface includes a relatively low-basis-weight region, and a plurality of laterally space-apart, relatively high-basis-weight, pocket regions.

14. An apparatus as recited in claim 1, further comprising:

a forming chamber through which said forming surface is movable;

a fiber source which is configured to provide fibrous material into said forming chamber; and a vacuum generator which is configured to provide an operative, relatively lower pressure, vacuum condition in said vacuum-commutator duct system;

wherein said forming chamber has a selectively varied shape in at least regions of said forming chamber that are located proximate said forming surface; and said varied shape of the forming chamber cooperatively changes to approximately match a changing shape of said entrance opening of the vacuum-commutator duct.

15. An apparatus as recited in claim 1, wherein said vacuum-commutator duct system includes:

a first end wall member;

at least a second end wall member which is longitudinally spaced from said first end wall member;

a first side wall member which interconnects between said first and second end wall members; and at least a second side wall member which interconnects between said first and second end wall members and is laterally spaced from said first side wall member.

16. An apparatus as recited in claim 15, wherein said first and second end wall members are operatively attached to a vacuum conduit member which is configured to extend axially along a rotational axis of said forming drum.

17. A method for forming a fibrous web, which includes:

a providing of a movable, foraminous forming surface;

a providing of a substantially stationary, vacuum-commutator duct system which is located substantially subjacent said forming surface; and a configuring of said vacuum-commutator duct system to have an entrance opening that changes in shape along a longitudinal dimension of said entrance opening.

18. A method as recited in claim 17, which further includes a configuring of said vacuum-commutator duct system to have an entrance opening that changes in cross-directional width when moving along a longitudinal dimension of said entrance opening.

19. A method as recited in claim 17, which further includes a configuring of said forming surface to include a relatively low-basis-weight region, and at least one relatively high-basis-weight region.

a configuring of said entrance opening of the vacuum-commutator duct system to have a first opening section with a first lateral width, and at least a second opening section with a second lateral width, with said second lateral width differing from said first lateral width; and configuring said first lateral width of the entrance opening to operatively match a lateral width of said relatively high-basis-weight region of the forming surface.

20. A method as recited in claim 19, which further includes a configuring of said forming surface to include
a foraminous forming member;
a first circumferentially extending baffle; and
at least a second circumferentially extending baffle that is laterally spaced from said first circumferentially extending baffle;

a positioning of said first and second circumferential baffles subjacent said foraminous forming member;

a positioning of said first and second circumferentially extending baffles laterally adjacent said relatively high-basis-weight region of the forming surface;

a configuring of said vacuum-commutator duct system to include side wall members; and a positioning of said first and second circumferentially extending baffles to be substantially aligned with said side wall members of said vacuum-commutator duct system, as observed at said first opening section of the vacuum-commutator duct system.

\* \* \* \* \*